Figure 1:
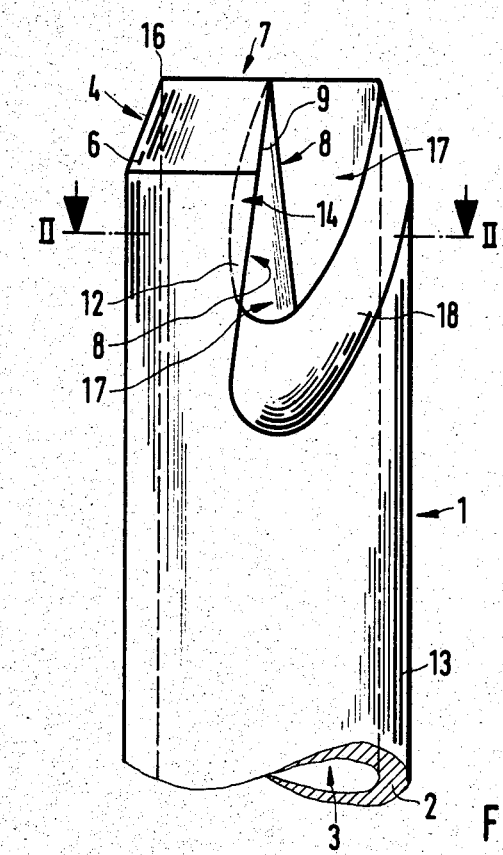

United States Patent [19]

Schnepp-Pesch et al.

[11] Patent Number: 4,640,296
[45] Date of Patent: Feb. 3, 1987

[54] BIOPSY CANNULA

[76] Inventors: Wolfram Schnepp-Pesch, Schönblick 6, D-7505 Ettlingen 8; Josef Lindenberg, Buchenweg 13, D-7512 Rheinstetten 4, both of Fed. Rep. of Germany

[21] Appl. No.: 807,248

[22] Filed: Dec. 10, 1985

Related U.S. Application Data

[63] Continuation of Ser. No. 570,501, Jan. 13, 1984, abandoned.

[30] Foreign Application Priority Data

Nov. 12, 1983 [DE] Fed. Rep. of Germany ....... 3341117

[51] Int. Cl.⁴ .............................................. A61B 10/00
[52] U.S. Cl. .................................................. 128/754
[58] Field of Search ................................. 128/751–754, 128/757–758, 310, 304, 305–305.1; 30/90, 95, 113.1; 604/22, 239, 272–274

[56] References Cited

U.S. PATENT DOCUMENTS

| | | | |
|---|---|---|---|
| 3,606,721 | 9/1971 | Hallac | 128/754 |
| 3,628,524 | 12/1971 | Jamshidt | 128/754 |
| 3,683,892 | 8/1972 | Harris | 128/754 |
| 3,990,451 | 11/1976 | Gibbs | 128/754 |
| 4,362,161 | 12/1982 | Reimals et al. | 128/310 |

FOREIGN PATENT DOCUMENTS

| | | | |
|---|---|---|---|
| 149464 | 7/1981 | German Democratic Rep. | 128/755 |
| 197709 | 9/1977 | U.S.S.R. | 128/754 |

Primary Examiner—William E. Kamm
Attorney, Agent, or Firm—Antonelli, Terry & Wands

[57] ABSTRACT

A biopsy needle for avoiding major lesions to be biopsied and destruction of tissue cells which includes a cannula having a cylindrical jacket wall surrounding an axially extending hollow space for receiving a tissue specimen and at least one blade having the cutting extending from an insert surface of the cylindrical jacket wall diagonally toward the outside in a direction of a cutting edge.

6 Claims, 2 Drawing Figures

U.S. Patent  Feb. 3, 1987  4,640,296

BIOPSY CANNULA

This is a continuation of application Ser. No. 570,501, filed Jan. 13, 1984, now abandoned.

This invention relates to a cannula for biopsies having a cylinder jacket wall surrounding an axial hollow space for receiving a tissue specimen and having at least one blade with two cutting sides ending, at an acute angle, in a cutting edge.

Biopsy sets serve for the removal of tissue specimens from, for example, the kidneys, the prostate gland, the breast, the liver or the lungs, for histological examination. To carry out a biopsy, at least one biopsy needle is used consisting of a cannula and a pointed blade. In the case of a known biopsy needle, the pointed blade has a fairly long notch in the area of its front end. The point is formed by a sloping of the end of the pointed blade. The cannula also has a sloped end with a rounded-off blade at the most extreme end. The biopsy is carried out by inserting the biopsy needle either to in front of or into the tissue to be removed while the pointed blade is largely drawn into the cannula. Subsequently, the notch is exposed by either pulling back the cannula or by further advancing the pointed blade. Thus, the notch is exposed so that tissue can enter into it from the side. The tissue that has entered into the notch is cut off by pushing the cannula over the notch. Subsequently, the whole biopsy needle is withdrawn in closed condition. Reliable work can be carried out by means of this biopsy needle when a sufficient amount of tissue can be removed without major danger with respect to a destruction of cells. However, because of the weakening of the pointed blade caused by the presence of the notch, the diameter of the pointed blade and thus of the whole needle must be quite large and is in the range of almost 2 mm. Considerable lesions are therefore caused during the biopsy in the organs or the tissue where the biopsy is to be carried out, resulting in hematomas. A biopsy in which this known needle is used is very painful for the patient with the result being that patients tend to avoid necessary biopsies.

In another biopsy set, the biopsy needle has a pointed blade with a sharpened end and a typical cannula which, in its end area, corresponding to the shape of the point of the blade, on its outer circumference, is provided with three sloped contact surfaces. This pointed shape of the cannula serves a better insertion together with the pointed blade because in this case, a practically uniform inserted point in the shape of a triangular pyramid is formed from the cannula to the pointed blade. This Chiba biopsy needle is used for the so-called Menghini suction biopsy. In this case, the pointed blade, after the needle is inserted, is taken out of the cannula. Subsequently, the cannula is provided with a suction syringe at its most extreme end which is drawn up sucking small pieces of tissue into the needle. It is true that the needle, because of the way it is used, can be selected to be quite thin and may have a diameter in the range of less than 1 mm; however, when the small pieces of tissue are sucked in, whole cells are drawn in only more or less randomly. On the other hand, there is considerable danger that cells may be destroyed which results in considerable risks, especially in the case of malignant cells.

This invention is therefore based on the objective of creating a cannula for biopsy needles which, while avoiding the mentioned disadvantages of the shown state of the art, can be developed with the smallest diameter but, at the same time, permits the removal of a sufficient, cleanly cut tissue specimen without the danger of a destruction of cells.

According to the invention, the mentioned objective is achieved by means of a biopsy cannula of the initially mentioned type which is developed in such a way that the blade has at least one cutting side extending from the inside surface diagonally toward the outside in the direction of the outside surfaces of the cylinder jacket wall. The core of the invention is therefore that, as was always the case previously, in addition to the needles, also the cannulas, on their outer circumference, were not only ground to a desired shape, but that, in contrast, the cannula, at its effective front end, is provided with an inside ground section, that therefore not the outside surface of the cylinder jacket of the cannula is ground, but that the inside circumference or the inside surfaces of the cannula is/are ground internally which results in the formation of a cutting edge. In this case, in order to produce a desired cutting edge, the outside circumference may also be slightly ground. However, it is significant that by the grinding of the inside wall, one cutting edge is displaced far toward the outside circumference. In a preferred embodiment, it is provided that the cutting side extending from the inside to the outside extends tangentially from the inside surface of the cylinder jacket wall. Consequently, in the area of the outside circumference, an optimal blade is achieved by means of, on the one hand, the cutting side that is ground from the inside to the outside, on the other hand, by means of the second cutting side formed by the outer circumference and the cutting edge in which the two cutting sides run together. In this case, the cutting edge laterally delimits a recess, the opposite limiting surface of which, the cylinder jacket wall may extend in parallel to the internally ground cutting side permitting an extremely simple manufacturing in one operational step. However, the wall surface that is opposite the cutting side and delimits the recess may also be ground in the desired manner, for example, in a shape that facilitates a certain entering of biopsied tissue laterally into the recess that is adjacent to the cutting edge. While according to a preferred embodiment, the cutting edge extends essentially in parallel to the axis, it is in an extremely preferred development slightly sloped in such a way that an undercutting has practically been provided, and the angle between the circumferential front edge of the cannula and the cutting edge is less than 90°, preferably in the range of about 95°.

For use with the cannula according to the invention, a conventional pointed blade may be used, for example, of the type that is used with the Chiba biopsy needle, even though, in the case where it has, at its front face, a ring-shaped edge extending in one plane vertically to the axis and especially where it is, at its front end, developed in the shape of the jacket of a truncated cone, a blade with a point that is ground to a truncated-cone shape should be preferred.

The cannula according to the invention is used as follows: The biopsy needle consisting of the cannula according to the invention and a corresponding pointed blade, when the pointed blade is completely pushed in, is inserted through the patient's skin into the area from which the biopsy is to be taken. Then the pointed blade is pulled out of the cannula and a suction syringe is applied at the extreme end of the cannula. This suction syringe is slightly drawn up so that a slight subpressure is created in the cannula. It is important that it is not drawn up so far that through the subpressure alone pieces of tissue are sucked into the cannula, as in the case of the Menghini suction biopsy. For this purpose, it is advantageous that the suction syringe, in a known manner, has markings or stops so that, in each case, as a function of the diameter of the cannula, the plunger of the suction syringe is pulled out by only a predetermined distance and thus only a slight predetermined subpressure is generated. Subsequently, the cannula according to the invention, with an applied slight subpressure, while it is turned, is pushed slightly toward the front, and by means of the turning, the cutting edge that is developed according to the invention continuously spirally cuts tissue from the organ to be biopsied and because of the subpressure, the cut tissue is sucked into the cannula. Then the cannula is pulled out.

Other advantages and characteristics of the invention are shown in the claims and in the following description in which one embodiment of the cannula according to the invention is described in detail.

Figure 2:
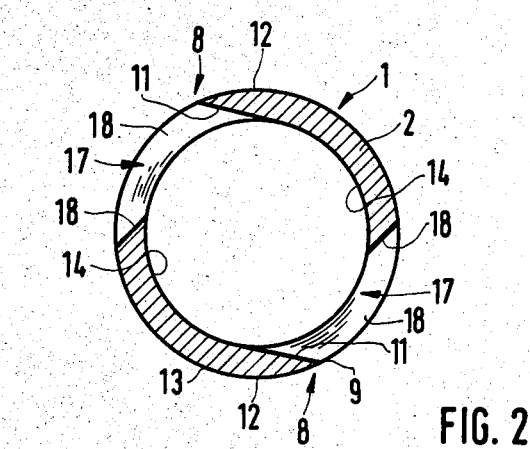

FIG. 1 is a lateral view of an end of the cannula according to the invention; and FIG. 2 shows a section along Line II—II of the cannula according to FIG. 1.

As shown in FIGS. 1 and 2 a cannula generally designated by the reference numeral 1 includes a body part having a cylinder jacket wall 2 surrounding an axial hollow space generally designated by the reference numeral 3. At its front or distal end generally designated by the reference numeral 4, the cannula 1 tapers conically in the shape of a truncated cone 6. Two blades generally designated by the reference numeral 8 which are formed diametrically in the cylinder jacket wall 2 of the cannula 1 extend from the front side generally designated by the reference numeral 7 of the cannula 1 essentially in axial direction with a very slight slope toward the axis of the cannula 1. The blades 8 are formed by two cutting sides 11, 12 which approach one another at an acute angle and end in a cutting edge 9. In this case, the cutting side 12 is part of the outside surface 13 of the cylinder jacket wall 2, while the inside cutting side 11 is a ground surface which extends tangentially from the inside surface 14 of the cylinder jacket wall 2 and continues toward the outside until it intersects the outside surface of the cylinder jacket wall 13 and thus the outside cutting side 12 in the cutting edge 9. Thus, the blade 12 is formed on the outer circumference of the cylinder jacket wall 2 of the cannula 1. As mentioned before, the cutting edge 9 does not extend precisely axially but to an axial generating line encloses an angle of a few degrees, i.e., up to 5° because of the fact that the cutting edge is sloped back from the front side 7 with respect to a line, that is, parallel to the axis, in the direction of the jacket 2. Therefore the ring-shaped front edge 16 of the cutting cannula 1 and the cutting edge 8 do not enclose an angle of 90° but an angle of somewhat below 90°. This improves the cutting of the cutting edge in the area of the front side 7 of the cannula 1.

At an axial side, the blade 8 in each case delimits a recess 17 in the cylinder jacket wall 2 of the cannula 1, in which case the recess 17 at the front side 7 of the cannula 1 is open and is otherwise delimited by ground wall surfaces 18 connecting the outside surface and the inside surface. As is shown especially in FIG. 1, the wall surfaces 18 in this case are ground in an arc-shaped manner. The blade 8, and thus the cutting edge 9 and the cutting side 11, may be ground together with the recess 17 and the other wall parts 18 delimiting it. In addition, other individual processing or grinding steps may be carried out on the cutting edge, on the one hand, and on the wall surface 18 that is opposite the cutting edge 11, on the other hand.

The cannula according to the invention, as shown in FIGS. 1 and 2, is used as follows as a part of the biopsy set:

The cannula 1 according to the invention, together with a pointed blade that can be inserted into it, forms a biopsy needle. At the front end of the cannula 1 shown in FIGS. 1 and 2, the pointed blade slightly projects from said cannula 1. The described biopsy needle unit, after a suitable anaesthesia, is inserted so far through a patient's skin by the physician until the front end 7 of the cannula 7 reaches into the tissue to be biopsied, in which case the insertion process is observed by means of ultrasound and can therefore be targeted by ultrasound. Subsequently, the pointed blade is taken out of the cannula, and the cannula, at its most extreme end (not shown) is connected with a vacuum suction device, most simply, with the plunger-cylinder part of a syringe. This syringe, in order to generate a subpressure in the cannula 1, is then drawn up slightly. For this purpose, it may have indicators and stopping mechanisms, by means of which, if necessary, as a function of the thickness of the needle, the distance of the drawing-up of the plunger and thus the amount of the produced subpressure is indicated or limited. Then, in the case of the embodiment shown in the drawings, the cannula under a slight pressure is turned clockwise. Thus, by means of the blade 8, a thin cylindrical strip of tissue is cut out of the tissue to be biopsied and is, on the one hand, by the slight advance and, on the other hand, by the subpressure in the cannula 1, pulled into said cannula 1. This process may also be observed by means of ultrasound and can thus be carried out with the highest precision. After a sufficiently long strip of tissue has been cut out and was pulled into the cannula 1, the cannula 1 is simply pulled out of the patient's body. The cut out tissue that is to be examined is then slowly pushed out of the cannula by pressing the plunger of the syringe or similar device carefully back into the cylinder part, pushing the tissue out of the end 7 of the cannula 1. It can then be subjected to the conventional histological examinations. The cannula according to the invention makes it possible to cut an extremely thin strip of tissue from the area to be biopsied without destroying cells resulting in possibly disadvantageous consequences and without, on the other hand, causing major lesions that may leave hematomas or similar effects in the biopsied tissue. By means of the cannula according to the invention, a biopsy can be carried out that subjects the patient to considerably less pain than in the case of the cutting-out of tissue that is pulled into the recess of an obturator, but does not result in the danger of a destruction of cells as in the case of the Menghini suction biopsy.

The characteristics of the invention disclosed in the above description, in the drawings and in the claims may be important for the realization of the inventive idea either individually as well as in suitable combinations.

We claim:

1. A biopsy cannula comprising a cylindrical jacket wall surrounding an axial hollow space for receiving a tissue specimen, a distal end of the cannula being conically tapered to form a substantially ring-shaped cutting edge, at least one axially extending recess provided at the distal end and opening in a direction of the distal end, at least one cutting side extending substantially tangentially from an inside surface of the cylindrical jacket wall toward an outside surface thereof, and at least one cutting edge extending substantially parallel to a longitudinal axis of the cannula provided on at least one side of the recess, the cutting edge being formed by a cutting side of the cylindrical jacket wall whereby the cutting edge is disposed in the outer periphery of the cylindrical jacket wall.

2. A cannula according to claim 1, wherein the at least one cutting edge extending substantially parallel to the longitudinal axis of the cannula and a plane in which the substantially ring-shaped cutting edge exists subtends an angle of less than 90°.

3. A cannula according to claim 1, wherein an angle of slope of the at least one cutting edge extending substantially parallel to the longitudinal axis of the cannula to a line at the cylindrical jacket wall which is parallel to the longitudinal axis of the cannula is about 5°.

4. A cannula according to claim 1, wherein at least two cutting edges extending substantially parallel to the longitudinal axis of the cannula are provided and are disposed diametrically opposite to one another.

5. A cannula according to claim 1, wherein the at least one longitudinally extending recess has a breadth that is about one fourth of a circumference of the cylindrical jacket wall.

6. A cannula according to claim 1, wherein the at least one longitudinally extending recess includes a wall connecting an inside surface of the substantially cylindrical jacket to an outside surface thereof, the wall being disposed opposite to the at least one cutting edge and extending in parallel to the cutting side.

* * * * *